(12) United States Patent
Tai et al.

(10) Patent No.: US 7,629,797 B2
(45) Date of Patent: Dec. 8, 2009

(54) RESONANCE-INDUCED SENSITIVITY ENHANCEMENT METHOD FOR CONDUCTIVITY SENSORS

(75) Inventors: Yu-Chong Tai, Pasadena, CA (US); Chi-yuan Shih, Pasadena, CA (US); Wei Li, Monterey Park, CA (US); Siyang Zheng, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 285 days.

(21) Appl. No.: 11/697,060

(22) Filed: Apr. 5, 2007

(65) Prior Publication Data

US 2007/0247173 A1    Oct. 25, 2007

Related U.S. Application Data

(60) Provisional application No. 60/789,510, filed on Apr. 5, 2006.

(51) Int. Cl.
 *G01R 27/26*  (2006.01)
(52) U.S. Cl. ................ 324/684; 324/686; 324/663; 324/664
(58) Field of Classification Search ................ 324/684, 324/686, 663, 664, 708
See application file for complete search history.

(56) References Cited

U.S. PATENT DOCUMENTS 3,545,271 A * 12/1970 Amir et al. ............... 73/861.41
6,204,734 B1 * 3/2001 Zhang et al. ............. 331/117 R
6,562,012 B1 * 5/2003 Brown et al. ................ 604/253
6,592,525 B2 * 7/2003 Miller et al. ................ 600/459
7,312,611 B1 * 12/2007 Harrison et al. ............ 324/453
7,492,167 B2 * 2/2009 Reich et al. ................ 324/663
2002/0118005 A1 * 8/2002 Reich et al. ................ 324/71.4

OTHER PUBLICATIONS

Zemann et al., Contactless Conductivity Detection for Capillary Electrophoresis, Analytical Chemistry, Feb. 1, 1998, pp. 563-567, vol. 70, No. 3.
Shih et al., A Novel Embedded Liquid Chromatography System with Submicron . . . , presented at 20th Int'l Symposium on Microscale Bioseparations, Amsterdam, the Netherlands, 2006.

* cited by examiner

*Primary Examiner*—Vincent Q Nguyen
*Assistant Examiner*—John Zhu
(74) *Attorney, Agent, or Firm*—Milestein Zhang & Wu LLC; Joseph B. Milstein

(57) ABSTRACT

Methods and systems for improving the sensitivity of a variety of conductivity sensing devices, in particular capacitively-coupled contactless conductivity detectors. A parallel inductor is added to the conductivity sensor. The sensor with the parallel inductor is operated at a resonant frequency of the equivalent circuit model. At the resonant frequency, parasitic capacitances that are either in series or in parallel with the conductance (and possibly a series resistance) is substantially removed from the equivalent circuit, leaving a purely resistive impedance. An appreciably higher sensor sensitivity results. Experimental verification shows that sensitivity improvements of the order of 10,000-fold are possible. Examples of detecting particulates with high precision by application of the apparatus and methods of operation are described.

18 Claims, 10 Drawing Sheets

RESONANCE-INDUCED SENSITIVITY ENHANCEMENT METHOD FOR CONDUCTIVITY SENSORS

CROSS-REFERENCE TO RELATED APPLICATIONS

This application claims priority to and the benefit of co-pending U.S. provisional patent application Ser. No. 60/789,510, filed Apr. 5, 2006, which application is incorporated herein by reference in its entirety.

STATEMENT REGARDING FEDERALLY FUNDED RESEARCH OR DEVELOPMENT

The invention described herein was made in the performance of work under National Science Foundation Grant No. CCR-0121778 and under NASA Grant No. NCC 9-58, and is subject to the provisions of Public Law 96-517 (35 U.S.C. §202) in which the Contractor has elected to retain title.

FIELD OF THE INVENTION

The invention relates to conductivity sensors in general and particularly to a conductivity sensor that employs components to counteract unwanted electrical characteristics.

BACKGROUND OF THE INVENTION

Electrical impedance sensing has been used to measure biological materials, such as tissue samples and cell suspensions for over a hundred years. It has been used in bulk hemacytometers and flow cytometers extensively. The direct current (DC) resistive sensing extends to alternating current (AC) impedance sensing. At low AC frequency (under 100 kHz), the signal is determined mainly by the cell volume. At higher frequency (100 kHz to 10 MHz), the intracellular structures also contribute to the overall measured impedance and become explorable measurands.

A serious problem in AC impedance sensing of particles (e.g., blood cells in plasma) with micro electrodes is that with the shrinking of electrode surface area the electrode double layer capacitance decreases. The double layer capacitance is in series with the channel impedance to be measured and it dominates the system impedance in the low frequency range. In high frequency, the stray capacitance which is in parallel with the channel impedance becomes the dominant part in system impedance. Stray capacitance can arise from, non-ideal electrode to electrode isolation. In AC impedance sensing of particles, the measurement device is limited to a frequency range, which is high enough to bypass electrode double layer impedance and low enough that the stray capacitance does not play a significant role in overall system impedance. As the electrodes are reduced in size, the frequency range dominated by the double layer capacitance expands to higher frequency. As a result, the sensitivity for particle sensing decreases.

Conductivity sensing is a technique widely used in fields such as liquid chromatography (LC), capillary electrophoresis (CE), cytometry, and cell impedance analysis to analyze or detect the concentration or presence of the analytes of interest. It is often desirable to improve conductivity sensor sensitivity especially for the cases where the analytes concentrations are extremely low or the intrinsic sensor sensitivities are low due to design limitations. For example, the sensitivity of the capacitively-coupled contactless conductivity detector ($C^4D$) is inferior to the conventional conductivity detector due to the fact that the sensing electrodes for $C^4D$ are covered by a protection layer and are not in direct contact with the electrolyte solution. While the $C^4D$ provides great advantages such as electrode robustness, the lower sensitivity certainly limits its application. It is often desirable to have a higher conductivity sensing sensitivity than can presently be attained, especially for the cases where the sensing electrodes are not in direct contact with the electrolyte solution. Therefore, there is a need to develop techniques that can enhance $C^4D$ sensitivity.

SUMMARY OF THE INVENTION

In one aspect, the invention relates to a method of increasing the sensitivity of a capacitively-coupled contactless conductivity detector. The method comprises the steps of: providing a capacitively-coupled contactless conductivity detector operable at an operation frequency $W_0$, the capacitively-coupled contactless conductivity detector comprising at least two electrodes disposed about a closed channel of an HPLC apparatus and spaced apart from each other, the capacitively-coupled contactless conductivity detector having a capacitance $C_W$ between the sensing electrode and a solution in the closed channel, a parasitic capacitance $C_P$ between the at least two electrodes, and a solution resistance $R_S$ between the at least two electrodes; and providing a inductor having an inductance $L_S$ and an internal serial resistance of $R_{LS}$ in parallel electrical connection with the capacitively-coupled contactless conductivity detector, the inductance $L_S$ selected to provide a substantially purely resistive impedance when in parallel combination with the capacitively-coupled contactless conductivity detector at the operation frequency $W_0$; measuring with the capacitively-coupled contactless conductivity detector a signal relating to an analyte-bearing fluid situated in the closed channel; analyzing the signal with an analysis module to extract a parameter of the analyte-bearing fluid; and recording the parameter in a memory for future use. The method thereby provides a capacitively-coupled contactless conductivity detector that exhibits enhanced sensitivity at the operation frequency $W_0$ as compared to the capacitively-coupled contactless conductivity detector without the parallel inductor.

In one embodiment, the capacitively-coupled contactless conductivity detector and the parallel inductor are fabricated on a monolithic substrate. In one embodiment, the monolithic substrate comprises silicon. In one embodiment, the inductor is an active inductor. In one embodiment, the method further comprises the step of adding a series resistance to the parallel combination of the capacitively-coupled contactless conductivity detector and the parallel inductor. In one embodiment, the step of adding a series resistance comprises adding a negative resistance.

In another aspect, the invention features a method of increasing the sensitivity of a capacitively-coupled contactless conductivity detector. The method comprises the steps of: providing a capacitively-coupled contactless conductivity detector, the capacitively-coupled contactless conductivity detector comprising at least two electrodes disposed about a closed channel of an HPLC apparatus mid spaced apart from each other, the capacitively-coupled contactless conductivity detector having a capacitance $C_W$ between the sensing electrode and a solution in the closed channel, a parasitic capacitance $C_P$ between the at least two electrodes, and a solution resistance $R_S$ between the at least two electrodes; providing a inductor having an inductance $L_S$ and an internal serial resistance of $R_{LS}$ in parallel electrical connection with the capacitively-coupled contactless conductivity detector, the inductance $L_S$ selected to provide a substantially purely resistive impedance when in parallel combination with the capacitively-coupled contactless conductivity detector; and operating the combination of the capacitively-coupled contactless conductivity detector and the parallel inductor at or close to a frequency $W_0$ given by $$W_0 = \frac{1}{\sqrt{2}} \left( \sqrt{\frac{1}{C_P C_{W'}^2 L_S^2 R_S^2} \left( \frac{-C_P L_S^2 - C_{W'} L_S^2 +}{C_{W'}^2 R_S^2 (L_S - C_P R_{LS}^2)} \right) + \sqrt{\frac{-4 C_P C_{W'}^2 L_S^2 R_S^2 (-L_S + (C_P + C_{W'}) R_{LS}^2 +}{(C_{W'} L_S (L_S - C_{W'} R_S^2) + C_P (L_S^2 + C_{W'}^2 R_S^2 R_{LS}^2))^2}} \right)$$

to measure a signal relating to an analyte-bearing fluid situated in the closed channel; analyzing the signal with an analysis module to extract a parameter of the analyte-bearing fluid; and recording the parameter in a memory for future use. The method thereby provides a capacitively-coupled contactless conductivity detector that exhibits enhanced sensitivity at or close to the operation frequency $W_0$ as compared to the capacitively-coupled contactless conductivity detector without the parallel inductor.

In one embodiment, the capacitively-coupled contactless conductivity detector and the parallel inductor are fabricated on a monolithic substrate. In one embodiment, the monolithic substrate comprises silicon. In one embodiment, the inductor is an active inductor. In one embodiment, the method further comprises the step of adding a series resistance to the parallel combination of the capacitively-coupled contactless conductivity detector and the parallel inductor. In one embodiment, the step of adding a series resistance comprises adding a negative resistance.

In yet another aspect, the invention provides a capacitively-coupled contactless conductivity detector having increased sensitivity. The capacitively-coupled contactless conductivity detector comprises: a capacitively-coupled contactless conductivity detector operable at an operation frequency $W_0$, the capacitively-coupled contactless conductivity detector comprising at least two electrodes disposed about a closed channel of an HPLC apparatus and spaced apart from each other, the capacitively-coupled contactless conductivity detector having a capacitance $C_{W'}$ between the sensing electrode and a solution in the closed channel, a parasitic capacitance $C_P$ between the at least two electrodes, and a solution resistance $R_S$ between the at least two electrodes; and a inductor having an inductance $L_S$ and an internal serial resistance of odes in parallel electrical connection with the capacitively-coupled contactless conductivity detector, the inductance $L_S$ selected to provide a substantially purely resistive impedance when in parallel combination with the capacitively-coupled contactless conductivity detector at the operation frequency $W_0$. The invention thereby provides a capacitively-coupled contactless conductivity detector that exhibits enhanced sensitivity at the operation frequency $W_0$ as compared to the capacitively-coupled contactless conductivity detector without the parallel inductor.

In one embodiment, the capacitively-coupled contactless conductivity detector and the parallel inductor are fabricated on a monolithic substrate. In one embodiment, the monolithic substrate comprises silicon. In one embodiment, the inductor is an active inductor. In one embodiment, the capacitively-coupled contactless conductivity detector further comprises a resistance in series with the parallel combination of the capacitively-coupled contactless conductivity detector and the parallel inductor. In one embodiment, the series resistance comprises a negative resistance.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 17 is a diagram illustrating a "negative resistance" element.

DETAILED DESCRIPTION OF THE INVENTION

Figure 1:
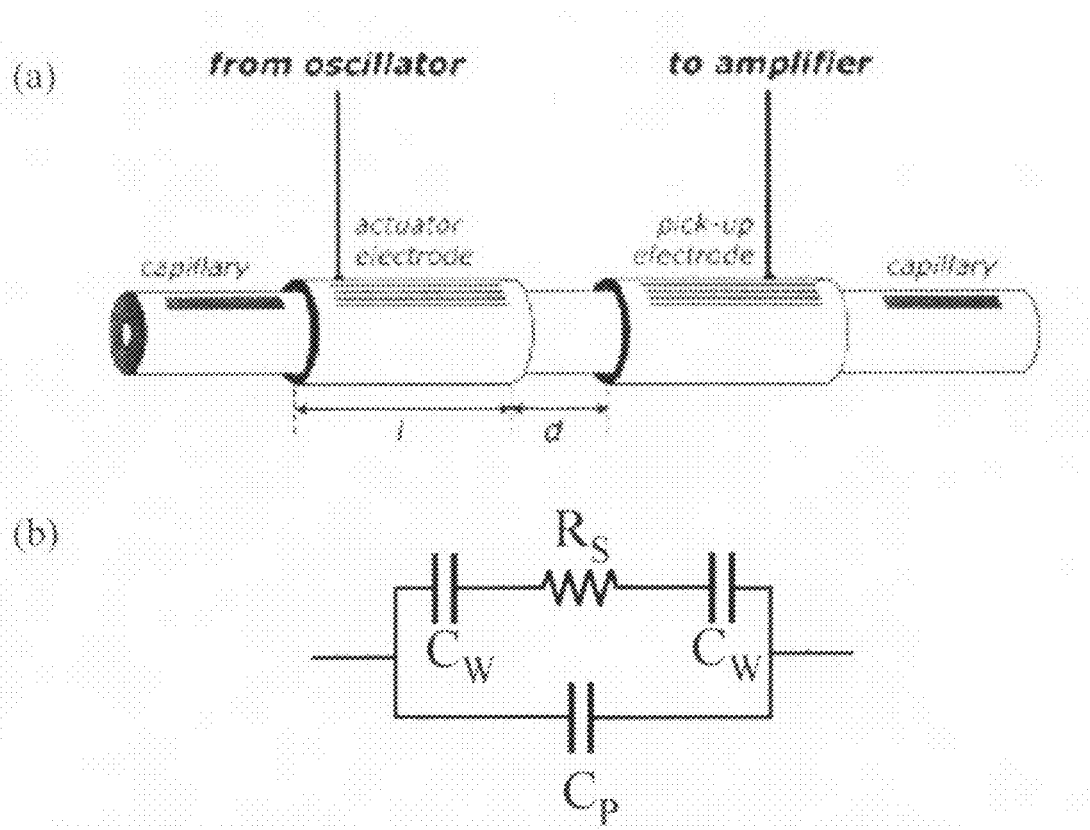
FIG. 1(a) is a diagram that shows in perspective schematic illustration a prior art capillary $C^4D$ system having sensing electrodes disposed outside of a flow channel.
FIG. 1(b) is a diagram that shows the equivalent circuit model of the $C^4D$ components of the prior art capillary $C^4D$ system of FIG. 1(a).

Capacitively-coupled contactless conductivity detection ($C^4D$) is a technique used frequently in LC and CE. In the conventional method, the sensing electrodes are put outside of a flow channel, such as the separation column in LC, as shown in FIG. 1(a) to avoid electrode corrosion by the solution flowing in the channel, such as an electrolyte solution. In the equivalent circuit model of $C^4D$, shown in FIG. 1(b), $C_W$ is the capacitance between the sensing electrode and the solution where the capillary wall material is the capacitor dielectric. $C_P$ is the parasitic capacitance between the electrodes. $R_S$ is the solution resistance between the electrodes.

Figure 2:
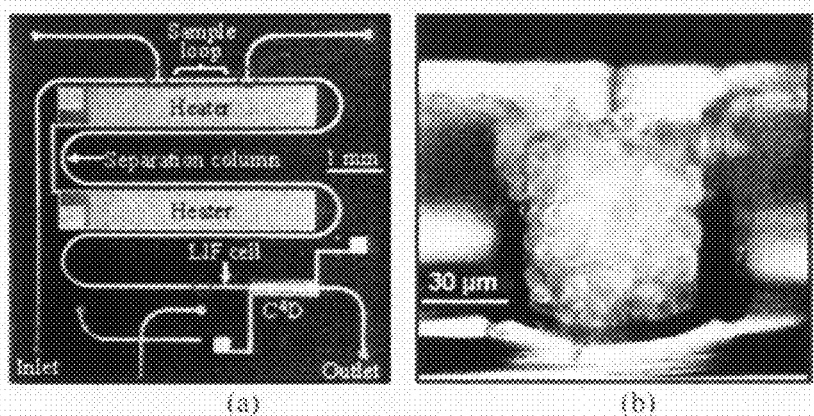
FIG. 2(a) is a diagram showing a top view of a temperature-controlled microchip high performance liquid chromatography (HPLC) system.
FIG. 2(b) is a diagram showing a cross section of a particle-packed HPLC column of a temperature-controlled microchip HPLC system such as that shown in FIG. 2(a).
Figure 3:
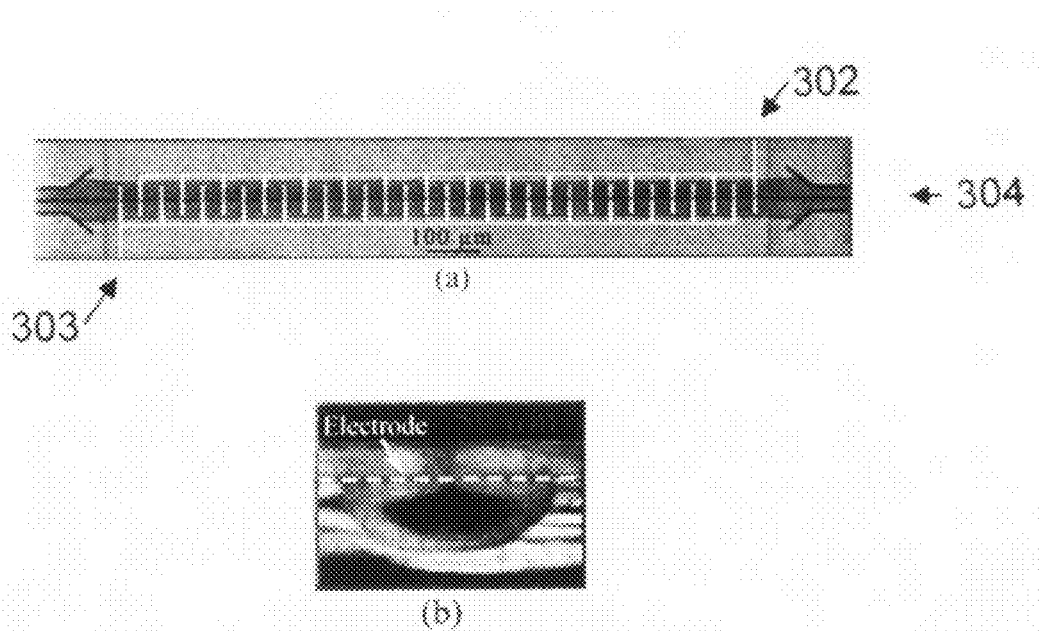
FIG. 3(a) is a diagram illustrating in top or plan view a $C^4D$ cell for analyte detection in a microchip HPLC system.
FIG. 3(b) is a diagram illustrating a $C^4D$ microfluidic channel cross-section.

The sensitivity degradation of conventional $C^4D$ is exacerbated when the sensor is built in micro scale devices such as those constructed using microfabrication technology such as MEMS. For example, FIG. 2(a) shows a temperature-controlled microchip HPLC (high performance liquid chromatography) system fabricated in the Caltech Micromachining Group laboratory that comprises a particle-packed liquid chromatography (LC) column, a 5 nL sample loop, a resistive heater, a laser-induced fluorescence (LIF) analyte detection port, and a $C^4D$ cell for ionic analytes detection. The fabricated $C^4D$ cell comprises interdigitated electrodes 302, 303 that are on top of a silicon dioxide layer and is further encapsulated by parylene coating as shown in FIG. 3. FIG. 3(a) is a diagram illustrating in top or plan view a $C^4D$ cell for analyte detection in a microchip HPLC system. Silicon underneath the $C^4D$ electrodes was etched away by $XeF_2$ etching to create a microfluidic channel cross-section 304. Electrical routing and contact pad area outside the sensing zone was minimized to reduce the parasitic capacitance. FIG. 3(b) is a diagram illustrating a $C^4D$ microfluidic channel cross-section. FIG. 3(c) shows the equivalent circuit model of the $C^4D$ cell. $C_W$ is the capacitance between the interdigitated electrodes and the solution where the oxide/parylene layer is the capacitor dielectric. $C_W$ was calculated to be 63 fF. $R_S$ is the solvent resistance between the interdigitated electrodes. In general, $R_S$ has a resistance ranging between 1 kΩ to 1 MΩ when the sensor is filled with the electrolyte solution. $C_P$ is the parasitic capacitance between the electrodes including fingers, routings, and contact pads. The capacitance of $C_P$ was measured using an HP4192A impedance analyzer to be 1.92 pF.

For high $C^4D$ sensitivity, $R_S$ should dominate the overall cell impedance. However, for the microchip $C^4D$ system, as compared to a macro scale capillary $C^4D$, $R_S$ is small due to the short distance between electrodes. $C_W$ is also small. Therefore there is a large impedance as a consequence of the small interdigitated electrode area. $C_P$ is large and therefore there is a small impedance as a consequence of the large electrical contact pads and the semi-conducting silicon substrate underneath the 1 μm-thick oxide layer. Therefore, the conventional microchip $C^4D$ sensitivity is expected to be much lower than that of the macro scale capillary $C^4D$ or than that of a microchip conductivity sensor where electrodes are in contact with the analyte solution. As used herein, the term microchip is also to be understood as denoting a monolithic substrate, such as a silicon chips or some other substrate upon which devices of the type herein contemplated can be fabricated.

In the conventional method, the sensitivity of $C^4D$ is degraded by the impedances of $C_W$ and $C_P$ which are in series and in parallel with the solution resistance $R_S$, respectively. In the microchip $C^4D$ system as shown in FIG. 3(a) and FIG. 3(b), the sensitivity is even worse. In other words, $R_S$ is small due to the short distance between electrodes, $C_W$ is small (therefore large impedance) due to the small interdigitated electrodes area, $C_P$ is large (therefore small impedance) due to the large size electrical contact pads and the silicon substrate.

Figure 4:
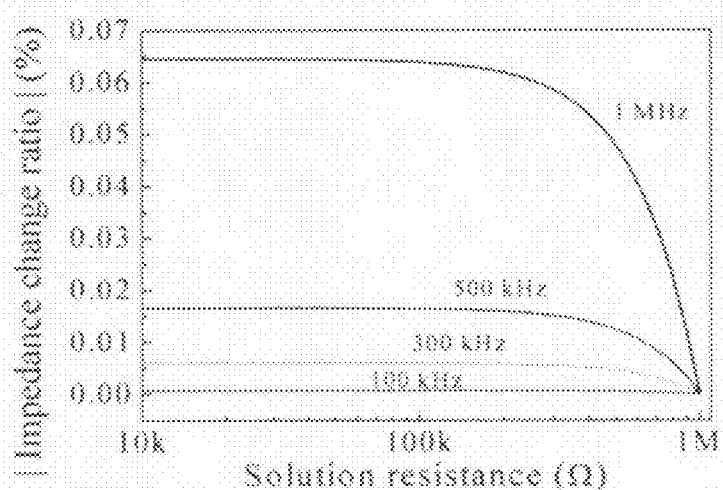
FIG. 4 is a diagram showing the results of an impedance analysis of the conventional $C^4$ cell.

FIG. 4 is a diagram that shows the simulation analysis of the conventional microchip $C^4D$ impedance based on its equivalent circuit model and component values mentioned earlier. Results indicate that even at 1 MHz sensing frequency, the cell impedance magnitude changes by less than 0.1% when the solution resistance changes from 1 MΩ to 10 kΩ.

To provide a solution to this measurement problem, we use resonant sensing by connecting an external parallel inductor to the system. At the resonant frequency, the inherent capacitive component in the system is nullified by the inductor, leaving the channel impedance (composed of electrolyte and particle impedance) dominant in the system. In some embodiments, the resonant excitation frequency can be selected by changing the inductance value. We explain the principles of operation of the RISE method or technique hereinbelow. We also provide examples in which the RISE technique has been applied to improve measurement sensitivity. As one example, we sensed 5 μm polystyrene bead. In another examples we successfully sensed blood cells in diluted human whole blood and leukocyte rich plasma. This technique so applied enabled us to directly measure the histogram of the contained cells. The results matched well with known volume histograms of erythrocytes and leukocytes.

Principle of Operation

Figure 5:
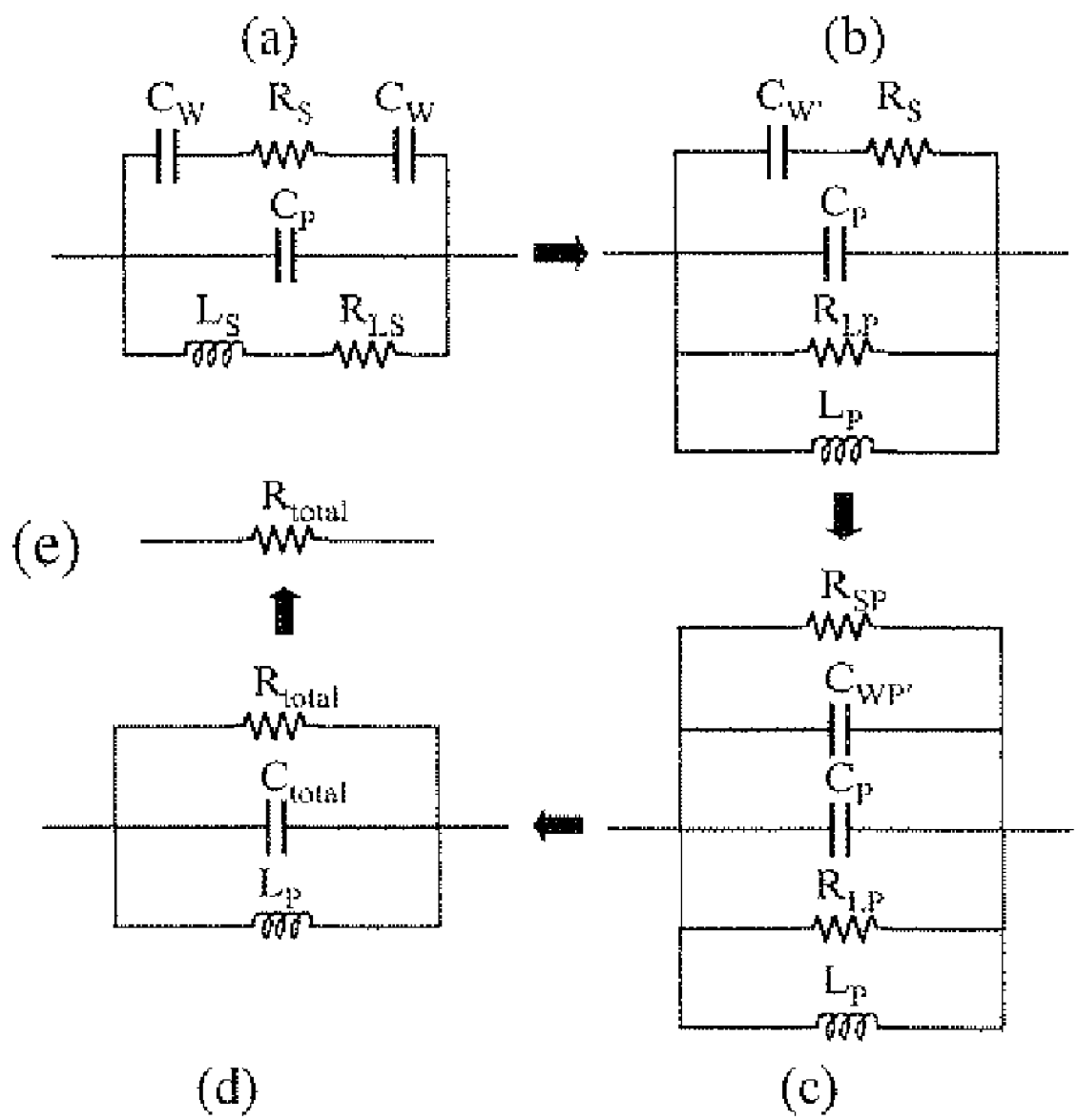
FIG. 5(a) through FIG. 5(d) are circuit diagrams useful to explain the principle of the RISE method.

The principle of the resonance-induced sensitivity enhancement (RISE) method is now described with reference to FIG. 5(a) through FIG. 5(e). An inductor $L_S$ with an internal serial resistance of $R_{LS}$ is put in parallel with the $C^4D$ cell as shown in FIG. 5(a). The serial circuit of $L_S$ and $R_{LS}$ can be transformed to an equivalent parallel circuit as shown in FIG. 5(b) that comprises a resistor $R_{LP}$ and an inductor $L_P$ according to the following equations (1):

$$Q_{LR} = \frac{W_0 L_S}{R_{LS}} \qquad (1)$$

$$L_P = L_S\left(\frac{Q_{LR}^2 + 1}{Q_{LR}^2}\right)$$

$$R_{LP} = R_{LS}(Q_{LR}^2 + 1)$$

where the operation frequency $W_0$ will be further discussed later. The two parylene wall capacitors $C_W$ are combined and become $C_{W'}$, according to equation (2):

$$C_{W'} = \frac{C_W}{2} \quad (2)$$

Then, the serial circuit of $C_{W'}$ and $R_S$ can be transformed to an equivalent parallel circuit as shown in FIG. 5(c) that comprises a resistor $R_{SP}$ and a capacitance $C_{WP'}$ according to the following equations (3):

$$Q_{CR} = \frac{1}{R_S W_0 C_{W'}} \quad (3)$$

$$C_{WP'} = C_{W'}\left(\frac{Q_{CR}^2}{Q_{CR}^2+1}\right)$$

$$R_{SP} = R_S(Q_{CR}^2+1)$$

As shown in FIG. 5(d), the resistance $R_{SP}$ and $R_{LP}$ are combined into $R_{total}$ and the capacitance $C_{WP'}$ and $C_P$ are combined into $C_{total}$ according to equations (4):

$$R_{total} = R_{SP} // R_{LP}$$

$$C_{total} = C_P + C_{WP'} \quad (4)$$

In one embodiment, the operation frequency $W_0$ (the input signal frequency) is chosen so that $C_{total}$ and $L_P$ reach resonance and the overall impedance is (or appears to be) a substantially pure resistance which is $R_{total}$ as shown in FIG. 5(e). It will be shown that at this resonant frequency the $C^4D$ sensitivity is dramatically enhanced. The resonant frequency is derived in equations (5):

$$W_0 = \frac{1}{\sqrt{L_P C_{total}}} \quad (5)$$

$$= \frac{1}{\sqrt{L_S\left(\frac{Q_{LR}^2+1}{Q_{LR}^2}\right)\left(C_P + C_{W'}\left(\frac{Q_{CR}^2}{Q_{CR}^2+1}\right)\right)}}$$

$$\frac{1}{W_0^2} = L_S\left(\frac{Q_{LR}^2+1}{Q_{LR}^2}\right)\left(C_P + C_{W'}\left(\frac{Q_{CR}^2}{Q_{CR}^2+1}\right)\right)$$

$$= L_S\left(\frac{\left(\frac{W_0 L_S}{R_{LS}}\right)^2+1}{\left(\frac{W_0 L_S}{R_{LS}}\right)^2}\right)\left(C_P + C_{W'}\left(\frac{\left(\frac{1}{R_S W_0 C_{W'}}\right)^2}{\left(\frac{1}{R_S W_0 C_{W'}}\right)^2+1}\right)\right)$$

$$= \left(\frac{(W_0 L_S)^2 + R_{LS}^2}{W_0^2 L_S}\right)\left(C_P + \frac{C_{W'}}{1+(R_S W_0 C_{W'})^2}\right)$$

$W_0$ is then solved using Mathematica. After discarding the complex and negative solution, the only solution left is that given by equation (6):

$$W_0 = \frac{1}{\sqrt{2}}\left(\sqrt{\frac{1}{C_P C_{W'}^2 L_S^2 R_S^2}\left(\frac{-C_P L_S^2 - C_{W'} L_S^2 +}{C_{W'}^2 R_S^2(L_S - C_P R_{LS}^2)} + \right)} + \sqrt{-4 C_P C_{W'}^2 L_S^2 R_S^2(-L_S + (C_P + C_{W'})R_{LS}^2 + \left(\frac{C_{W'} L_S (L_S - C_{W'} R_S^2) +}{C_P(L_S^2 + C_{W'}^2 R_S^2 R_{LS}^2)}\right)^2}\right) \quad (6)$$

The overall impedance at the resonant frequency is derived as shown in equation (7):

$$R_{total} = \frac{R_{LP} R_{SP}}{R_{LP} + R_{SP}} \quad (7)$$

$$= \frac{R_{LS}(Q_{LR}^2+1)R_S(Q_{CR}^2+1)}{R_{LS}(Q_{LR}^2+1)+R_S(Q_{CR}^2+1)}$$

$$= \frac{R_{LS}\left(\left(\frac{W_0 L_S}{R_{LS}}\right)^2+1\right)R_S\left(\left(\frac{1}{R_S W_0 C_{W'}}\right)^2+1\right)}{R_{LS}\left(\left(\frac{W_0 L_S}{R_{LS}}\right)^2+1\right)+R_S\left(\left(\frac{1}{R_S W_0 C_{W'}}\right)^2+1\right)}$$

$$= \frac{(R_{LS}^2 + L_S^2 W_0^2)(1 + C_{W'}^2 R_S^2 W_0^2)}{R_{LS} + C_{W'}^2 R_S R_{LS}(R_S + R_{LS})W_0^2 + C_{W'}^2 L_S^2 R_S W_0^4}$$

In order to have $R_{total}$ strongly dependent on the solution resistance $R_S$, discrete component values, $L_S$ and $R_{LS}$, are chosen in a way that $R_{LP}$ is much larger than $R_{SP}$ so that $P_{total}$ is dominated by $R_{SP}$ which in turn has a strong dependence on $R_S$.

In operation, the capacitively-coupled contactless conductivity detector is operated to measure a signal relating to an analyte-bearing fluid situated in the closed channel of the measurement device, such as a HPLC. The signal obtained is analyzed with an analysis module to extract a parameter of the analyte-bearing fluid, such as a concentration of a substance, particle density per volume, particle size, particle distribution and simial types of information. The extracted parameter is recorded in a memory for future use. For example, in microprocessor based analysis modules, data can be recorded in a register in a microprocessor, in a cache memory in the microprocessor, in local memory such as semiconductor memory (e.g., SRAM, DRAM, ROM, EPROM), magnetic memory (e.g., floppy disc or hard disc) and/or optical memory (e.g., CD-ROM, DVD, HD-DVD), or in a remote memory such as a central database. Analysis modules can include a custom circuit, a general purpose programmable computer with suitable analysis software operating thereon (for example, LAB-VIEW software or custom software) or some combination of hardware and software.

Demonstration of the RISE Technique

Figure 6:
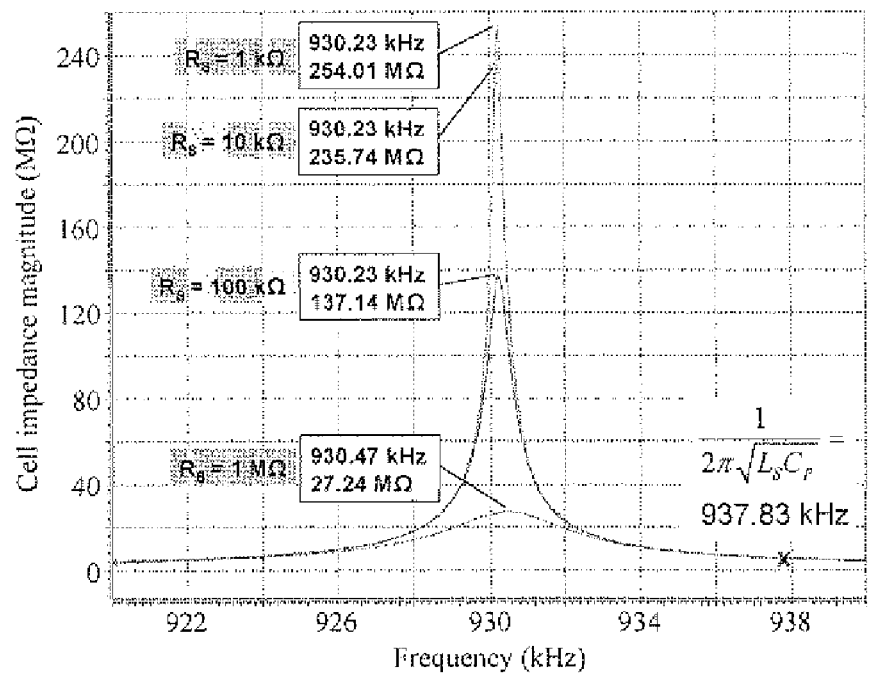
FIG. 6 is a diagram showing for a $C^4D$ cell constructed according to principles of the invention the results of HSPICE analysis of the $C^4D$ cell impedance magnitude versus frequency.

The performance of the RISE technique was demonstrated as follows. A discrete inductor having inductor component values of $L_S$ is 15 mH and $R_{LS}$ is 30 Ω were determined by measurement with the impedance analyzer. The microchip $C^4D$ component values were $C_W$=63 fF and $C_P$=1.92 pF. Using those component values, HSPICE analysis of the circuit was carried out. FIG. 6 shows the analysis results which are frequency scans of the cell impedance magnitude. Different curves were plotted for different solution resistance $R_S$ which is 1 kΩ, 10 kΩ, 100 kΩ and 1 MΩ, respectively.

The resonant frequencies extracted from the HSPICE results where the impedance magnitude curves reach the maxima match exactly with the calculated frequencies from the $\omega_0$ equation. It is also clear from FIG. 6 that at the resonant frequency (930.23 kHz), the cell impedance magnitude change ratio due to solution resistance change (from 1 MΩ to 1 kΩ) reaches its maximum. By comparison, if operating at the resonant frequency of $L_S$ and $C_P$ (937.83 kHz) there is virtually no impedance magnitude change.

Figure 7:
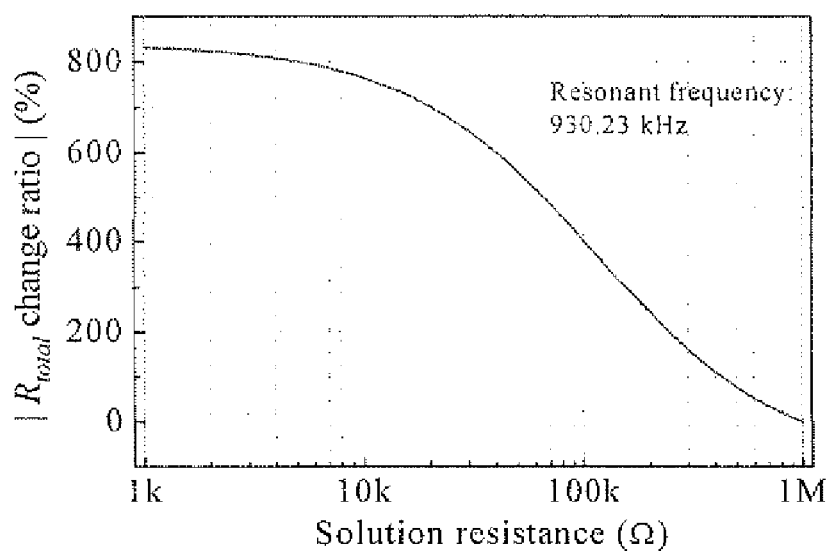
FIG. 7 is a diagram showing for a $C^4D$ cell constructed according to principles of the invention the results of a simulation of RISE-assisted microchip $C^4D$ performance.

The operation resonant frequency remains at 930.23 kHz for a solution resistance ranging from 1 kΩ to 100 kΩ and increases slightly to 930.47 kHz where the solution resistance is 1 MΩ. Since the resonant frequency is not sensitive to solution resistance in the designated solution resistance range, we chose the operation frequency $f_0$ to be 930.23 kHz or $\omega_0$ to be 5844.81 krad-Hz in the simulation that is discussed hereinbelow. As shown in FIG. 7, $R_{total}$ (total cell impedance at the resonant frequency) versus solution resistance $R_S$ curve is plotted. $R_{total}$ changes by 765% when the solution resistance changes from 1 MΩ to 10 kΩ. Compared with the native $C^4D$ performance demonstrated in FIG. 4, the sensitivity enhancement by RISE method is more than 10,000 times.

lution of the impedance analyzer prevented us from measuring the exact sensitivity enhancement ratio.

TABLE II

| | $L_S$ = 32 mH $R_{LS}$ = 16 kΩ $f_0$ = 633 kHz | | | |
|---|---|---|---|---|
| | Medium = air | Medium = DI water | Medium = 1M NaCl water | Impedance change ratio |
| Impedance magnitude (w/o RISE) | 130 kΩ | 129 kΩ | 130 kΩ | <1% |
| Impedance magnitude (with RISE) | 803 kΩ | 895 kΩ | 1127 kΩ | 40.3% |

TABLE I

| | | $C_W$ = 18.2 nF $C_P$ = 0.1 μF $L_S$ = 8.64 mH $R_{LS}$ = 78.8 Ω | | | | |
|---|---|---|---|---|---|---|
| | $f_0$ ($\omega_0/2\pi$) | $R_{total}$ (with RISE) ($R_S$ = 1000 Ω) | $R_{total}$ (with RISE) ($R_S$ = 1 Ω) | $|Z_{total}|$ (w/o RISE) ($R_S$ = 1000 Ω) | $|Z_{total}|$ (w/o RISE) ($R_S$ = 1 Ω) | Sensitivity Enhancement ratio |
| Theoretical values | 4.98 kHz | 939.7 Ω | 1004.9 Ω | 294.7 Ω | 292.9 Ω | 11.36 |
| Experimental results | 5.16 kHz | 940.4 Ω | 1004.7 Ω | 281.8 Ω | 280.0 Ω | 10.70 |
| Error | 3.61% | 0.07% | −0.02% | −4.38% | −4.40% | −5.81% |

Figure 8:
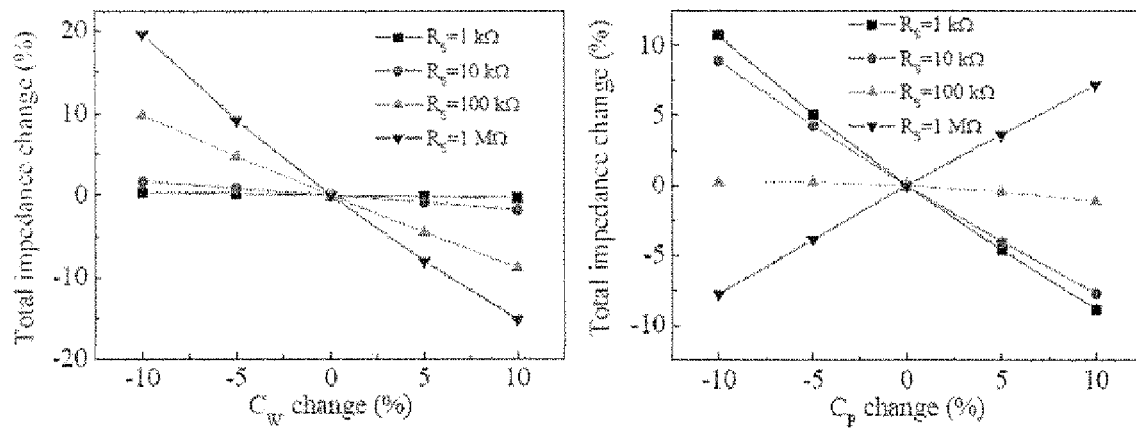
FIG. 8(a) is a diagram showing cell impedance fluctuation due to component value variations in $C_{W'}$ at an operating frequency of 930.23 kHz.
FIG. 8(b) is a diagram showing cell impedance fluctuation due to component value variations in $C_P$ at an operating frequency of 930.23 kHz.

It is clear that the resonance-induced sensitivity enhancement technique makes our C4D sensitive enough for conductivity sensing in microchip HPLC. FIG. 8(a) and FIG. 8(b) show the measured results of cell impedance fluctuation caused by component value changes. FIG. 8(a) is a diagram showing cell impedance fluctuation due to component value variations in $C_W$, at an operating frequency of 930.23 kHz. FIG. 8(b) is a diagram showing cell impedance fluctuation due to component value variations in $C_P$ at an operating frequency of 930.23 kHz.

As a first step to verify the RISE technique experimentally, a model RISE-assisted $C^4D$ circuit was built with discrete resistors, inductors, and capacitors. Component values were: $C_W$=18.2 nf, $C_P$=0.1 μf; $L_S$=8.64 mh; $R_{LS}$=78.8 Ω; $R_S$=1 or 1,000 Ω. $R_{total}$ was measured for different $R_S$ values under the resonant frequency $\omega_0$ where the circuit impedance magnitude maximized. $|Z_{total}|$ is the measured impedance magnitude of the native $C^4D$ circuit (no $L_S$ and $R_{LS}$) at the frequency $\omega_0$. The experimental results in TABLE I show extremely good matching between theoretical and experimental values, and are an experimental verification of RISE method using a model circuit built with discrete components.

We then applied the RISE technique to our microchip $C^4D$ device to verify the sensitivity enhancement performance. In this experiment, $L_S$ is 32 mH and $R_{LS}$ is 16 kΩ. As shown in TABLE II, media of different electrical conductivities (air, DI water, and 1M NaCl water solution) were flowed through the $C^4D$ microfluidic channel and the cell impedance magnitude was recorded with and without RISE assistance. The resonant frequency was experimentally measured using the HP4192A impedance analyzer to be 633 kHz. These measured results showed that the RISE method significantly enhanced the microchip $C^4D$ sensitivity. We believe that the limited reso- RISE Method Optimization While the experimental results illustrated that the RISE method is capable of providing significant sensitivity enhancement for microchip $C^4D$, the RISE method can be further optimized with respect to specific sensing parameters as will be discussed hereinbelow.

First, for conventional coil inductors, the inductance is proportional to the square of the number of coil turns N, while the internal serial resistance is proportional to the number of coil turns, as shown in equations (8):

$$R_{LS} \propto N \propto \sqrt{L_S}$$

$$\text{or, } R_{LS} = A^* \sqrt{L_S}. \quad (8)$$

Using one set of the measured component values ($L_S$=15 mH and $R_{LS}$=30 Ω) we obtain the value of parameters A and $R_{LS}$ as shown in equations (9):

$$A = \frac{R_{LS}}{\sqrt{L_S}} = \frac{30}{\sqrt{15E-3}} \quad (9)$$

$$R_{LS} = 30\sqrt{L_{LS}/15E-3}.$$

The RISE-assisted $C^4D$ sensitivity $S_{RISE}$ is defined here as in equation (10):

$$S_{RISE} = \left| \frac{\partial R_{total}}{R_{total} \partial R_S} \right|. \quad (10)$$

Figure 9:
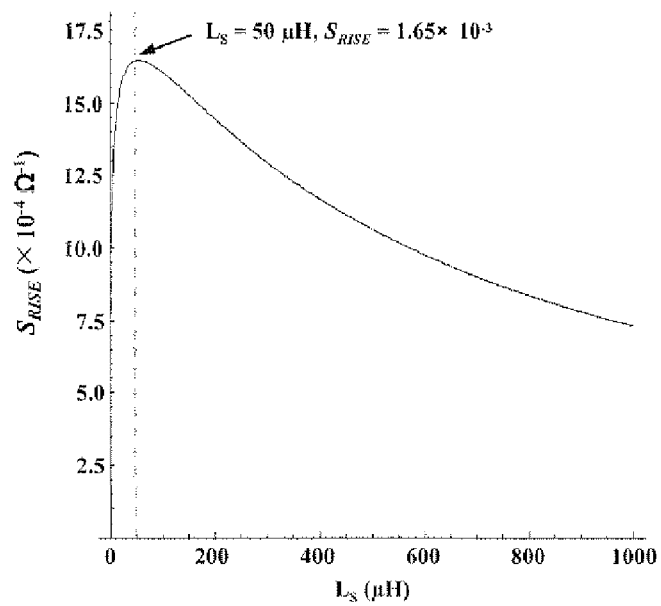
FIG. 9 is a diagram showing a graphical method of optimizing the sensitivity $S_{RISE}$ for $R_S$ equal to 1 MΩ.

Now, if we wish to optimize conductivity sensitivity for $R_S$ around 1 MΩ, we can plot $S_{RISE}$ versus inductance $L_S$ with $R_S$ equal to 1 MΩ and then locate the Ls value where $S_{RISE}$ is maximized. This is shown as an example in FIG. 9.

Another way to optimize RISE method is to maximize the $C^4D$ impedance change ratio $\gamma_{RISE}$ when $R_S$ changes from 1 MΩ to 1 kΩ, as shown in equation (11):

$$\gamma_{RISE} = \left| \frac{R_{total(R_S=1\,M\Omega)} - R_{total(R_S=1\,k\Omega)}}{R_{total(R_S=1\,M\Omega)}} \times 100\% \right|. \quad (11)$$

By plotting $\gamma_{RISE}$ versus $L_S$, the maximum ratio is found to be 2249% where $L_S$ is 600 μH. TABLE III shows a summary of the RISE performances with and without optimization.

TABLE III

|  | Without optimization | Optimized for impedance change ratio | Optimized for sensitivity | Enhancement ratio |
|---|---|---|---|---|
| Component values | $L_S$ = 15 mH<br>$R_{LS}$ = 30 Ω<br>$f_0$ = 930.23 kHz | $L_S$ = 600 μH<br>$R_{LS}$ = 6 Ω<br>$f_0$ = 4.65 MHz | $L_S$ = 50 μH<br>$R_{LS}$ = 1.73 Ω<br>$f_0$ = 16.11 MHz | N/A |
| $V_{RISE}$ | 832% | 2249% | N/A | 270.3% |
| $S_{RISE}$ | 8.02E−5 | N/A | 1.65E−3 | 2057% |

Figure 10:
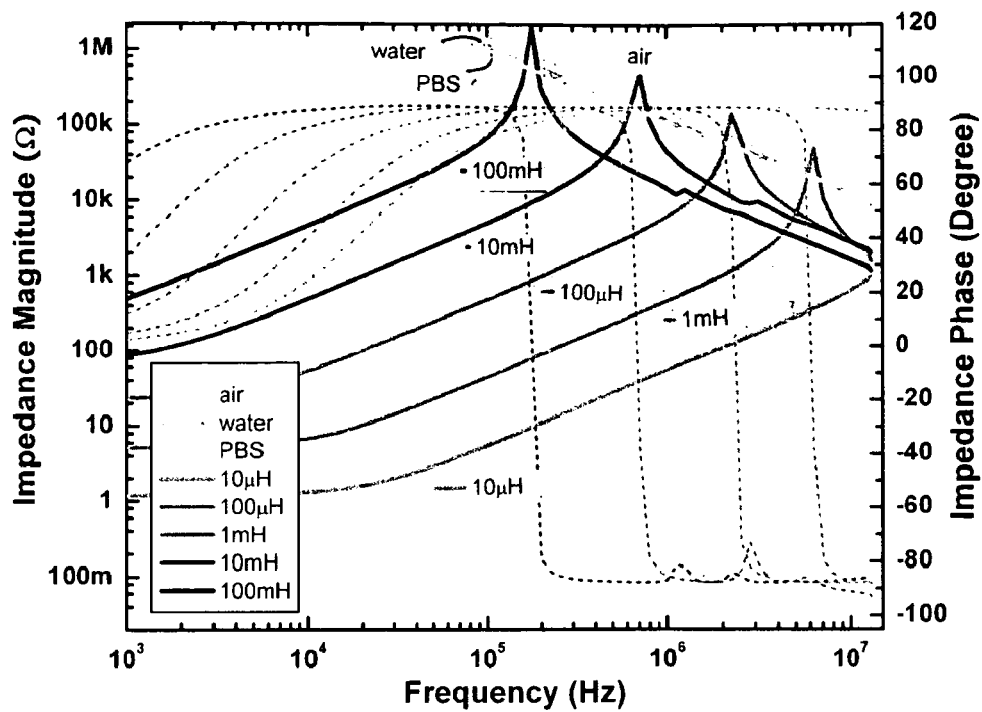
FIG. 10 is a diagram that shows measured impedance magnitude response (solid lines) and phase response (dot lines) in different environments and with parallel inductors of different values in PBS.

The principle of impedance particle sensing relies on the change of electrical impedance as a particle replaces electrolyte in the sensing zone. This impedance change was measured by a pair of electrodes separated by an aperture. Preferably the channel impedance (which is represented by channel resistance $R_s$ in low frequency) should be the dominant impedance of the system so that the signal is sensitive to the particle's existence. However, in conventional sensing systems comprising micro electrodes, the double layer surface capacitance $C_{dl}$ typically dominates the system impedance in low frequency and the stray capacitance $C_{st}$ dominates in high frequency. As a result, the frequency spectra of air, DI water and electrolyte PBS inside a device operating according to conventional measurement principles could not be distinguished, as shown in FIG. 10.

Figure 11:
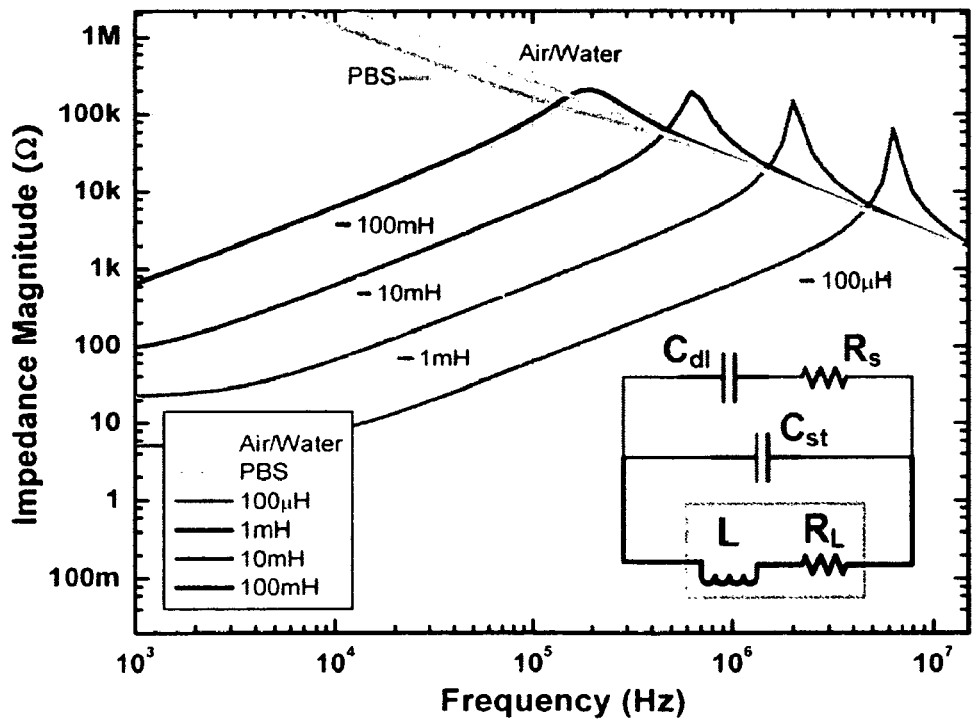
FIG. 11 is diagram that shows the results of a SPICE circuit simulation of impedance magnitude response, for an equivalent circuit shown in the inset.

Following the principles of the present invention, in which a parallel inductor is added to nullify the system capacitance components at the resonant frequency, a system with single resonant frequency was created. This system was analyzed using SPICE simulation as shown in FIG. 11, and its behavior was confirmed with measurement as shown in FIG. 10. With the addition of a parallel inductor, the system total impedance was most sensitive to the channel impedance change at the resonant frequency.

Device Fabrication

Figure 12:
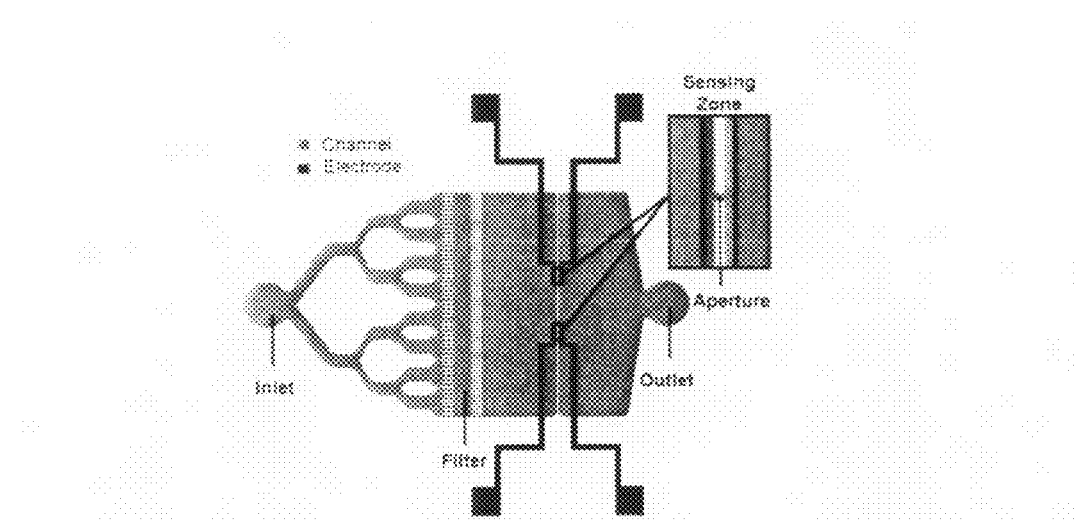
FIG. 12 is a diagram the shows in schematic form a layout of an embodiment of a device according to principles of the invention.

A device was made by bonding PDMS defined channels to glass with Ti/Pt patterned electrodes as shown in FIG. 12. Two parallel sensing zones were provided to double the system throughput and enable differential input to sensing circuitry to reduce drift and noise. In other embodiments, a single sensing zone could be employed, or a larger number than two sensing zones could be employed. The two fluidic chambers were separated by an aperture. In the embodiment described now, the width of the aperture was 14 μm. The length of the aperture was 20 μm. One pair of metal electrodes was used to sense the electrical impedance across one aperture. The size of the chamber was very large compared with the aperture so that the measured channel impedance was dominated by the impedance of the aperture region. The separation between the electrodes was 50 μm. At the inlet, some filter structures were designed to mechanically block contaminants and particle aggregates and prevent them from clogging the aperture. Channel height was approximately 15 μm so that all blood cells could pass while keeping the signal magnitude as high as possible. In the embodiment discussed now, conventional discrete coil inductors were used to demonstrate the application of the principle of the invention. However, if a sensing system according to principles of the invention is constructed as a monolithic device for example on a microchip, the inductors can also be fabricated on the microchip to provide an integrated solution. A lock-in amplification system (EG&G Princeton Applied Research Model 5210, available from EG&G Princeton Applied Research, Princeton, N.J.) with superior signal to noise ratio was used to track the system impedance change at resonant frequency.

Particle Sensing Results

Figure 13:
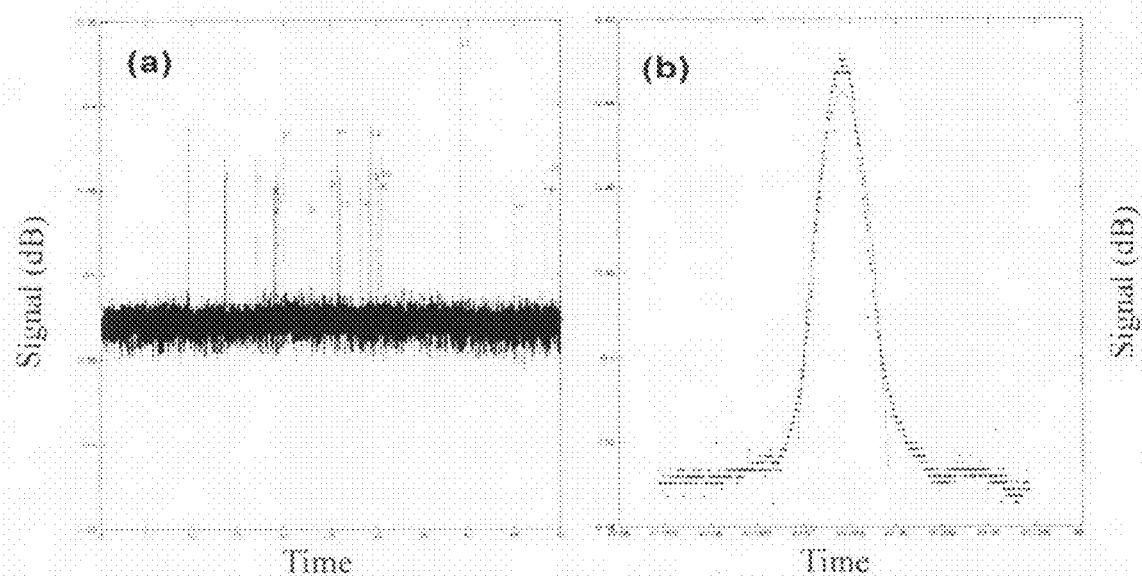
FIG. 13(a) is a diagram that shows a time trace obtained during sensing of 5 μm polystyrene beads at a resonant frequency 104 kHz.
FIG. 13(b) is a diagram that shows an example peak obtained during sensing of 5 μm polystyrene beads at resonant frequency 104 kHz.

Particle sensing was first validated with 5 μm diameter polystyrene beads at a resonant frequency of 104 kHz. The flow rate was 10 nL/min. The particle concentration was approximately 104 particles per μL. FIG. 13(a) shows an example of time trace of 5 μm polystyrene beads. The peak height was 0.058V±0.013V for a sample of 249 beads in one testing. The duration of the peaks was 37.8 ms±6.8 ms which corresponded well with the expected time that the beads passed the sensing zone. FIG. 13(b) is a typical peak from the same data set. Polystyrene beads of 8 μm and 10 μm diameter were also tested and the signal magnitude was found to increase with the size of the beads.

Figure 14:
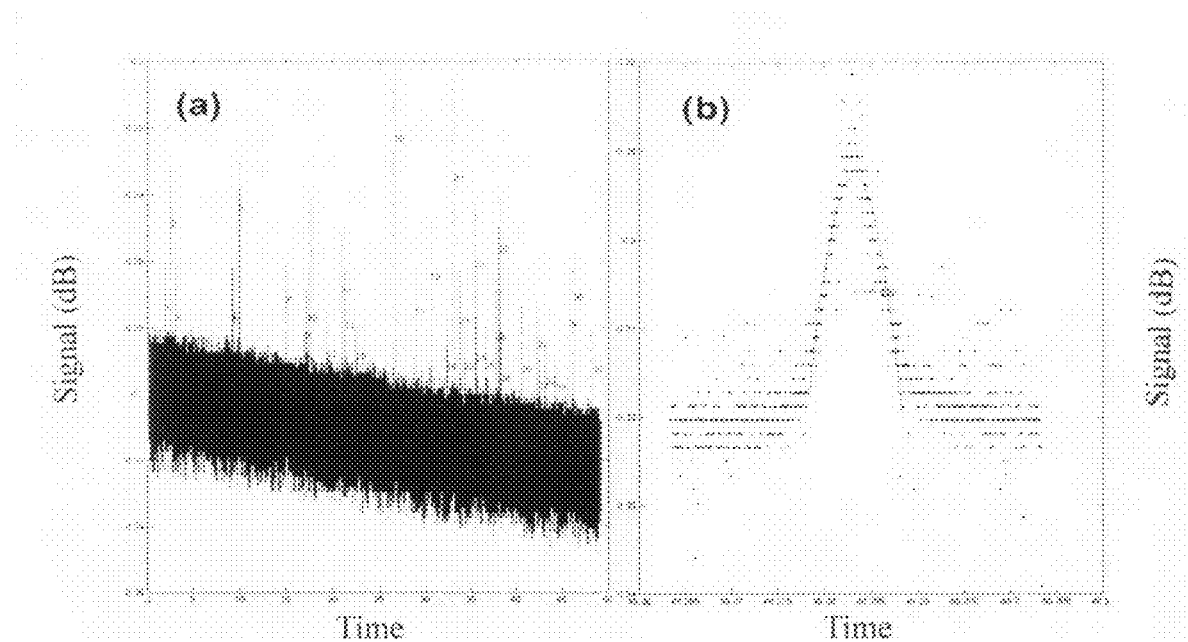
FIG. 14(a) is a diagram that shows a time trace obtained during sensing of diluted human whole blood at resonant frequency 90.8 kHz.
FIG. 14(b) is a diagram that shows an example peak obtained during sensing of diluted human whole blood at resonant frequency 90.8 kHz.

Human blood cell sensing was performed either with diluted whole blood or diluted leukocyte rich plasma. Whole blood samples were obtained from healthy donors and used within 48 hours. Normal whole blood has an erythrocyte to leukocyte ratio about one thousand to one. So it is good for erythrocyte characterization without leukocyte interference. Leukocyte rich plasma was prepared using the Wintrobe method. Erythrocyte to leukocyte ratio can be reduced by at least two orders of magnitude using this method, so the prepared samples are better for leukocyte testing. FIG. 14(a) shows a time trace for human whole blood diluted by one thousand times. A close-up of one single peak was shown in FIG. 14(b).

It is well known that under DC and low frequency AC excitation, the change of channel impedance is correlated to the volume of the particles including biological cells. Based on our system model and fitting parameters obtained from impedance spectra measurement, the volume of the particles was found be roughly linear with the change of total impedance magnitude at resonance, which was proportional to the peak height of the signal. Therefore, the distribution of impedance change can be used to measure the particle volume distribution.

Figure 15A:
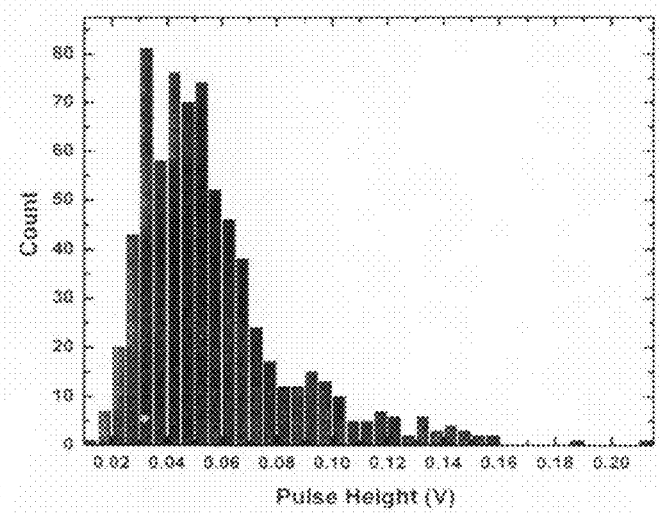
FIG. 15A is a diagram that shows the pulse height distribution of diluted human whole blood, in which leukocyte to erythrocyte ratio is about one to a thousand.
Figure 15B:
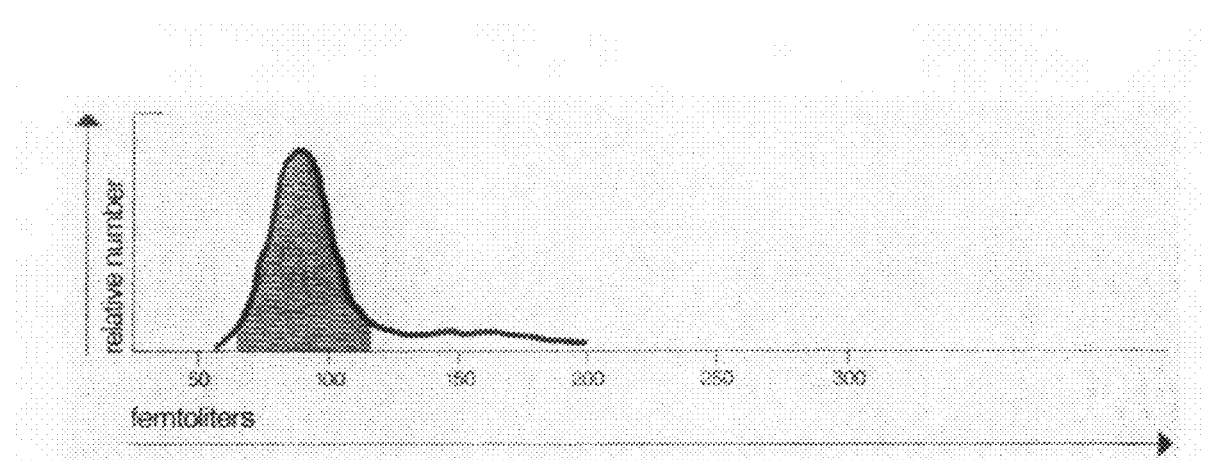
FIG. 15B is a diagram that shows an erythrocyte volume histogram from S. B. McKenzie, Clinical Laboratory Hematology: Prentice Hall, 2004.
Figure 16A:
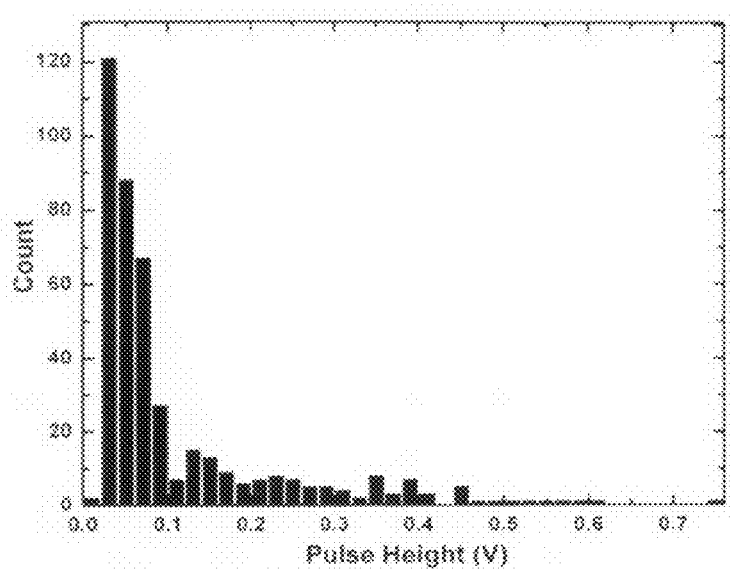
FIG. 16A is a diagram that shows the pulse height distribution of leukocyte rich plasma, in which leukocyte to erythrocyte ratio is about one to ten.
Figure 16B:
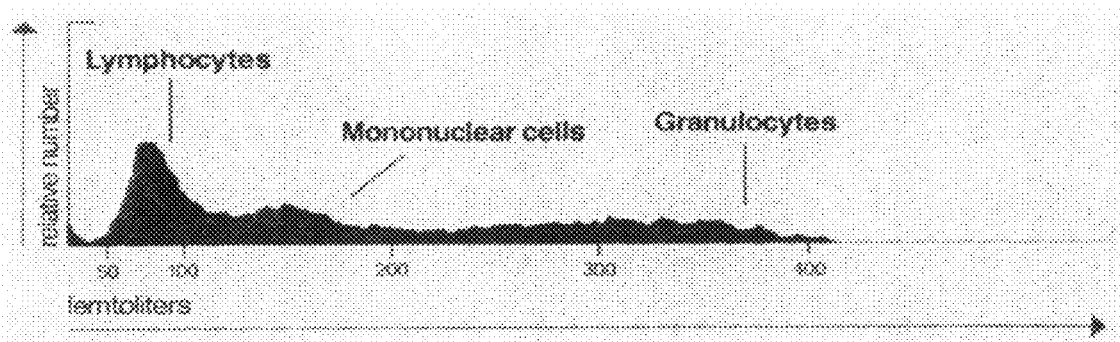
FIG. 16B is a diagram that shows a leukocyte volume histogram from S. B. McKenzie, Clinical Laboratory Hematology: Prentice Hall, 2004.

For diluted whole blood, the peak height of blood cell traces had a wide distribution which indicates that the cell size varied. The histogram of pulse height matched well with the known volume distribution of erythrocytes, as shown in FIG. 15. Leukocyte rich plasma was used for leukocyte sensing. The tail part of the peak height histogram was contributed mainly by leukocytes as shown in FIG. 16, while the small pulse height portion (under 0.1V) is presumably still dominated by erythrocytes. The tail part resembles the known leukocytes volume distribution.

ADDITIONAL POSSIBLE EMBODIMENTS

The proposed resonance-induced sensitivity enhancement technique can be used for versatile conductivity sensing applications. For example, other than microchip $C^4D$, it can be used with the conventional capillary $C^4D$ for sensitivity enhancement. It can also be used to enhance the sensitivity of general conductivity sensors where electrodes are in direct contact with the electrolyte solution. In this case, it is the double-layer capacitance on top of the electrodes and the parasitic capacitance between electrodes that will be removed from the equivalent circuit using RISE.

In some embodiments the introduced inductor can be fabricated together with the $C^4D$ sensors. For example, an on-chip inductor can be fabricated with metal thin-film/thick-film coils. In some embodiments, the inductor can be replaced with an active inductor (e.g., a circuit component exhibiting inductive characteristics) constructed from a combination of active devices, resistors, and capacitors. It is well known in the prior art that one can build devices that having inductive characteristics, but that comprise a combination of active devices, resistors, and capacitors. See Fig. B entitled "active inductor" at page 304 of the book "The Art of Electronics," $2^{nd}$ Edition, by Horowitz and Hill (Cambridge University Press, 1989, ISBN 0-521-37095-7). The circuit shown comprises three resistors, a capacitor and an operational amplifier (LF411), but no conventional inductor.

The conductance values can be chosen in a way that the resonant frequency is in the desirable level.

A series resistor can be put in series with the inductor to control the overall series resistance value. In some embodiments, a circuit element that behaves as a "negative resistance" can be employed to provide a desired total resistance. As an example, a "negative resistance element" is shown in FIG. 17.

A resonant-frequency-tuning mechanism such as putting a variable capacitance in parallel with the $C^4D$ sensor can be applied so to maintain the resonant frequency at a constant level. This mechanism might be necessary when the resonant frequency fluctuates due to external condition changes such as temperature, moisture, or electromagnetic interferences.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

We have explained the principles of and demonstrated the performance of the RISE technique to significantly enhance the sensitivity of conductivity sensors. The RISE technology is efficient, low-cost and easy to implement. It is important to understand that RISE can be applied to versatile conductivity sensing applications and not just to microchip $C^4D$ for HPLC analyte detection. For example, RISE can be applied to the conventional capillary HPLC or capillary electrophoresis (CE) systems to improve the macro-sized $C^4D$ sensitivity. It can also be used to enhance the sensitivity of conventional conductivity sensors where sensing electrodes are in direct contact with the electrolyte solution. In this case, it is the double-layer capacitance on top of the electrodes as well as the parasitic capacitance from electrode routing that will be substantially removed from the circuit using the RISE technology.

We have demonstrated that we can sense the presence of particles such as 5 µm polystyrene beads. We then demonstrated human erythrocytes and leukocytes sensing with this approach. The histograms of the signal magnitude matched well with previous published volume distributions of the erythrocytes and leukocytes. The advantages of downsizing electrodes and the sensing zone in micro devices include increased sensitivity, lowered sample dilution factor and thus increased system throughput. The sensing frequency can be flexibly selected by changing the parallel inductance.

Machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein.

While the present invention has been particularly shown and described with reference to the structure and methods disclosed herein and as illustrated in the drawings, it is not confined to the details set forth and this invention is intended to cover any modifications and changes as may come within the scope and spirit of the following claims.

What is claimed is:

1. A method of increasing the sensitivity of a capacitively-coupled contactless conductivity detector, comprising the steps of:
   providing a capacitively-coupled contactless conductivity detector operable at an operation frequency $W_0$, said capacitively-coupled contactless conductivity detector comprising at least two electrodes disposed about a closed channel of an HPLC apparatus and spaced apart from each other, said capacitively-coupled contactless conductivity detector having a capacitance $C_W$ between the sensing electrode and a solution in said closed channel, a parasitic capacitance $C_P$ between said at least two electrodes, and a solution resistance $R_S$ between the at least two electrodes;
   providing a inductor having an inductance $L_S$ and an internal serial resistance of $R_{LS}$ in parallel electrical connection with said capacitively-coupled contactless conductivity detector, said inductance $L_S$ selected to provide a substantially purely resistive impedance when in parallel combination with said capacitively-coupled contactless conductivity detector at said operation frequency $W_0$;
   measuring with said capacitively-coupled contactless conductivity detector a signal relating to an analyte-bearing fluid situated in said closed channel;
   analyzing said signal with an analysis module to extract a parameter of said analyte-bearing fluid; and
   recording said parameter in a memory for future use;
   thereby providing a capacitively-coupled contactless conductivity detector that exhibits enhanced sensitivity at said operation frequency $W_0$ as compared to said capacitively-coupled contactless conductivity detector without said parallel inductor.

2. The method of increasing the sensitivity of a capacitively-coupled contactless conductivity detector of claim 1, wherein said capacitively-coupled contactless conductivity detector and said parallel inductor are fabricated on a monolithic substrate.

3. The method of increasing the sensitivity of a capacitively-coupled contactless conductivity detector of claim 2, wherein said monolithic substrate comprises silicon.

4. The method of increasing the sensitivity of a capacitively-coupled contactless conductivity detector of claim 1, wherein said inductor is an active inductor.

5. The method of increasing the sensitivity of a capacitively-coupled contactless conductivity detector of claim 1, further comprising the step of adding a series resistance to said parallel combination of said capacitively-coupled contactless conductivity detector and said parallel inductor.

6. The method of increasing the sensitivity of a capacitively-coupled contactless conductivity detector of claim 5, wherein said step of adding a series resistance comprises adding a negative resistance.

7. A method of increasing the sensitivity of a capacitively-coupled contactless conductivity detector, comprising the steps of:
   providing a capacitively-coupled contactless conductivity detector, said capacitively-coupled contactless conductivity detector comprising at least two electrodes disposed about a closed channel of an HPLC apparatus and spaced apart from each other, said capacitively-coupled contactless conductivity detector having a capacitance $C_W$ between the sensing electrode and a solution in said closed channel, a parasitic capacitance $C_P$ between said at least two electrodes, and a solution resistance $R_S$ between the at least two electrodes;
   providing a inductor having an inductance $L_S$ and an internal serial resistance of $R_{LS}$, in parallel electrical connection with said capacitively-coupled contactless conductivity detector, said inductance $L_S$ selected to provide a substantially purely resistive impedance when in parallel combination with said capacitively-coupled contactless conductivity detector;
   operating said combination of said capacitively-coupled contactless conductivity detector and said parallel inductor at or close to a frequency $W_0$ given by $$W_0 = \frac{1}{\sqrt{2}} \left\{ \sqrt{\frac{1}{C_P C_{W'}^2 L_S^2 R_S^2}(-C_P L_S^2 - C_{W'} L_S^2 + C_{W'}^2 R_S^2 (L_S - C_P R_{LS}^2) + \sqrt{-4 C_P C_{W'}^2 L_S^2 R_S^2(-L_S + (C_P + C_{W'})R_{LS}^2 + (C_{W'} L_S(L_S - C_{W'} R_S^2) + C_P(L_S^2 + C_{W'}^2 R_S^2 R_{LS}^2))^2}} \right\}$$

to measure a signal relating to an analyte-bearing fluid situated in said closed channel;
   analyzing said signal with an analysis module to extract a parameter of said analyte-bearing fluid; and
   recording said parameter in a memory for future use;
   thereby providing a capacitively-coupled contactless conductivity detector that exhibits enhanced sensitivity at or close to said operation frequency $W_0$ as compared to said capacitively-coupled contactless conductivity detector without said parallel inductor.

8. The method of increasing the sensitivity of a capacitively-coupled contactless conductivity detector of claim 7, wherein said capacitively-coupled contactless conductivity detector and said parallel inductor are fabricated on a monolithic substrate.

9. The method of increasing the sensitivity of a capacitively-coupled contactless conductivity detector of claim 8, wherein said monolithic substrate comprises silicon.

10. The method of increasing the sensitivity of a capacitively-coupled contactless conductivity detector of claim 7, wherein said inductor is an active inductor.

11. The method of increasing the sensitivity of a capacitively-coupled contactless conductivity detector of claim 7, further comprising the step of adding a series resistance to said parallel combination of said capacitively-coupled contactless conductivity detector and said parallel inductor.

12. The method of increasing the sensitivity of a capacitively-coupled contactless conductivity detector of claim 11, wherein said step of adding a series resistance comprises adding a negative resistance.

13. A capacitively-coupled contactless conductivity detector having increased sensitivity, comprising:
   a capacitively-coupled contactless conductivity detector operable at an operation frequency $W_0$, said capacitively-coupled contactless conductivity detector comprising at least two electrodes disposed about a closed channel of an HPLC apparatus and spaced apart from each other, said capacitively-coupled contactless conductivity detector having a capacitance $C_W$ between the sensing electrode and a solution in said closed channel, a parasitic capacitance $C_P$ between said at least two electrodes, and a solution resistance $R_S$ between the at least two electrodes; and a inductor having an inductance $L_S$ and an internal serial resistance of $R_{LS}$ in parallel electrical connection with said capacitively-coupled contactless conductivity detector, said inductance $L_S$ selected to provide a substantially purely resistive impedance when in parallel combination with said capacitively-coupled contactless conductivity detector at said operation frequency $W_0$;

thereby providing a capacitively-coupled contactless conductivity detector that exhibits enhanced sensitivity at said operation frequency $W_0$ as compared to said capacitively-coupled contactless conductivity detector without said parallel inductor.

14. The capacitively-coupled contactless conductivity detector of claim 13, wherein said capacitively-coupled contactless conductivity detector and said parallel inductor are fabricated on a monolithic substrate.

15. The capacitively-coupled contactless conductivity detector of claim 14, wherein said monolithic substrate comprises silicon.

16. The capacitively-coupled contactless conductivity detector of claim 13, wherein said inductor is an active inductor.

17. The capacitively-coupled contactless conductivity detector of claim 13, further comprising a resistance in series with said parallel combination of said capacitively-coupled contactless conductivity detector and said parallel inductor.

18. The capacitively-coupled contactless conductivity detector of claim 17, wherein said series resistance comprises a negative resistance.

* * * * *